United States Patent [19]

Drake

[11] Patent Number: 5,270,048
[45] Date of Patent: Dec. 14, 1993

[54] CONTROLLED DELIVERY DEVICES

[75] Inventor: Cyril F. Drake, Harlow, United Kingdom

[73] Assignee: Borden (UK) Limited, Southampton, United Kingdom

[21] Appl. No.: 941,753

[22] Filed: Sep. 3, 1992

Related U.S. Application Data

[63] Continuation of Ser. No. 511,745, Apr. 20, 1990, abandoned.

[30] Foreign Application Priority Data

Apr. 21, 1989 [GB] United Kingdom ............... 8909046

[51] Int. Cl.⁵ .............................................. A61F 2/00
[52] U.S. Cl. ................................ 424/426; 424/400; 424/423; 424/438; 604/890.1
[58] Field of Search ............... 424/426, 423, 400, 438

[56] References Cited

U.S. PATENT DOCUMENTS 3,844,285 10/1974 Laby ................................... 128/260
4,449,981 5/1984 Drake ................................. 604/891

FOREIGN PATENT DOCUMENTS

0042219 12/1981 European Pat. Off. .
2164557 3/1986 United Kingdom .

Primary Examiner—Thurman K. Page
Assistant Examiner—D. Gabrielle Phelan
Attorney, Agent, or Firm—Burns, Doane, Swecker & Mathis

[57] ABSTRACT

A device for controllably delivering a material into an aqueous medium, the device comprising a soluble portion which is adapted, in use, to dissolve in an aqueous medium thereby to deliver into the aqueous medium a material which is retained in the device, the soluble portion comprising a soluble phosphate glass having a $P_2O_5$ content of from 40 to 50 mole %, and constraining means which are located in the vicinity of the soluble portion and which are arranged, in use, to constrain a stationary liquid layer between the soluble portion and the constraining means. The invention also relates to a method of controllably dissolving a soluble phosphate glass in an aqueous medium.

18 Claims, 9 Drawing Sheets

CONTROLLED DELIVERY DEVICES

This application is a continuation of application Ser. No. 07/511,745, filed Apr. 20, 1990, now abandoned.

BACKGROUND OF THE INVENTION

This invention relates to a device including a portion of phosphate glass which can be controllably dissolved to perform a function, for example to release controlled quantities of an active material into an aqueous environment at or after a pre-determined time interval. The invention also relates to a method for controlling the dissolution of a phosphate glass.

There is a need for the release of active materials such as drugs or pesticides into an aqueous environment at or after a pre-determined time after being placed in contact with the aqueous environment, or continuously at a predetermined rate. It is known to employ glasses which act as a barrier between the aqueous environment and the active material and which dissolve in the aqueous environment over a period of time thereby to release the active material at or after a pre-determined time Period. It is also known to employ such glasses which themselves incorporate the active material. Previous work in this field includes the work reported in UK-B-2057420 which dealt with the overall control of the dissolution of glasses and exemplified phosphate glasses with a $P_2O_5$ content in excess of 50 mole %.

The glasses disclosed in UK-B-2057420 suffer from the disadvantage that controlled dissolution of the glasses is not possible since, for glass compositions having greater than 50 mole % $P_2O_5$, the solution products are hindered from leaving the glass surface because there is a tendency for gelatinous films to form adjacent to the glass surface. The gelatinous films interfere with the dissolution of the glass and render the dissolution rate time - dependent i.e. the dissolution rate decreases with time. This means that the dissolution of the glass cannot be reliably controlled.

SUMMARY OF THE INVENTION

It is an aim of the present invention to enable reliably controlled release of an active material by controlled dissolution of a Phosphate glass.

Accordingly, in one aspect the present invention provides a device for controllably delivering a material into an aqueous medium, the device comprising a soluble portion which is adapted, in use, to dissolve in an aqueous medium thereby to deliver into the aqueous medium a material which is retained in the device, the soluble portion comprising a soluble phosphate glass having a $P_2O_5$ content of from 40 to 50 mole %, and constraining means which are located in the vicinity of the soluble portion and which are arranged, in use, to constrain a stationary liquid layer between the soluble portion and the contraining means.

In a second aspect, the present invention provides a method of controllably dissolving a soluble phosphate glass in an aqueous medium, the soluble phosphate glass having a $P_2O_5$ content of from 40 to 50 mole %, the method comprising disposing the soluble phosphate glass in the aqueous medium and locating constraining means in the vicinity of the portion thereby to constrain a stationary liquid layer therebetween.

The present invention is based on the discovery (a) that glasses containing from 40 to 50 mole % $P_2O_5$ dissolve in a controllable manner at certain concentration ranges of the dissolution products in the aqueous medium and (b) of the need to retain a uniform stationary layer of the aqueous medium at the dissolving surface from which solution products may diffuse in a controlled manner. This means that the devices according to the invention can take many forms so long as this basic requirement of the provision of a stationary liquid layer is met, and the phosphate glass used has a $P_2O_5$ content in the range from 40 to 50 mole %.

BRIEF DESCRIPTION OF THE DRAWINGS

Embodiments of the present invention will now be described by way of example only with reference to the accompanying drawings, in which.

DESCRIPTION OF THE PREFERRED EMBODIMENTS

In the devices of each of the three illustrated embodiments of the present invention, there is provided a specific means to retain a stationary liquid layer of controlled thickness adjacent to at least a portion of the soluble phosphate glass. In the following description of the embodiments of FIGS. 1 to 3, the means to retain the stationary liquid layer are initially described. The theory underlying, and the experimental data evidencing, the advantages of the present invention are subsequently described.

Figure 1:
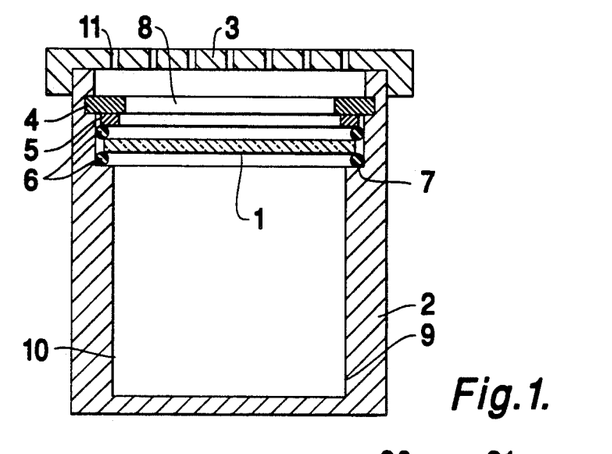
FIG. 1 is a vertical cross-sectional view of a device, in accordance with a first embodiment of the present invention, for the release of an active material in which a disc of phosphate glass is used as a means of controlling the elapsed time before the release of the active material.

FIG. 1 shows a form of a device in accordance with a first embodiment of the present invention in which a glass disc 1 is retained within a container 2 by means of a spring-clip 4 which transmits pressure via a washer 5 thereby to press the glass disc 1 between two elastomeric O-rings 6 against the shoulder 7 in the container 2. The container has an end wall 3. The glass disc 1 is composed of a soluble phosphate glass having a $P_2O_5$ content of from 40 to 50 mole %. O-rings 6 form a water-tight seal between a space 8 and body 9 of the container 2 which contains the agent 10 to be released. The glass disc 1 initially acts as a barrier between the agent 10 and the exterior of the device. As will be described hereinafter, the glass disc 1 is slowly dissolved by an aqueous medium in which the device is, in use, disposed. The end wall 3 of the container 2 is provided with holes 11 which allow diffusion of liquid and dissolution products from the space 8 next to the glass disc 1 to the exterior of the device and the end wall 3 acts to maintain a stationary liquid film between the end wall 3 and the glass disc 1 in which the concentration of dissolution products is maintained within a predetermined range. The dimensions of the upper O-ring 6, the washer 5 and the clip 4 are selected to give the desired thickness of stationary layer above the glass disc 1. Liquid and dissolution products can diffuse into the body of the liquid exterior of the device through the holes 11. The space 8 may be filled with filter paper which forms a permeable membrane which assists in ensuring that a stationary liquid film is maintained above the glass disc as it dissolves.

The devices of the present invention are of particular value in the pulsed release in ruminant animals of various materials which must otherwise be dispersed in the animals feed or supplied by periodic drenching or injection. Such active materials include anthelmintics and growth promoters. Many of these materials are insoluble in aqueous media and are therefore difficult to disperse uniformly in a feed mix. They must also be released in pulsed doses so that only sufficient material is released in the animal for its immediate needs.

In use, the device initially contains an active material such as an anthelmintic (i.e. a composition for killing worms in the rumen of ruminant animals). The device is inserted into the rumen of the animal, e.g. by swallowing. The water-based medium in the rumen surrounds the device and enters the space 8 through the holes 11. The glass disc 1 slowly dissolves into the aqueous medium in the stationary liquid layer so formed. The stationary liquid layer permits a controlled concentration gradient of dissolution products of prescribed thickness to be established which, in combination with the particular concentration of $P_2O_5$ in the glass being from 40 to 50 mole %, enables a substantially uniform dissolution rate of the material of the glass disc into the stationary liquid layer over a Period of time. After a prescribed period has elapsed, the glass disc is perforated as a result of the dissolution thereof thereby releasing the active material into the rumen of the animal.

Figures 2A, 2B, 2C:
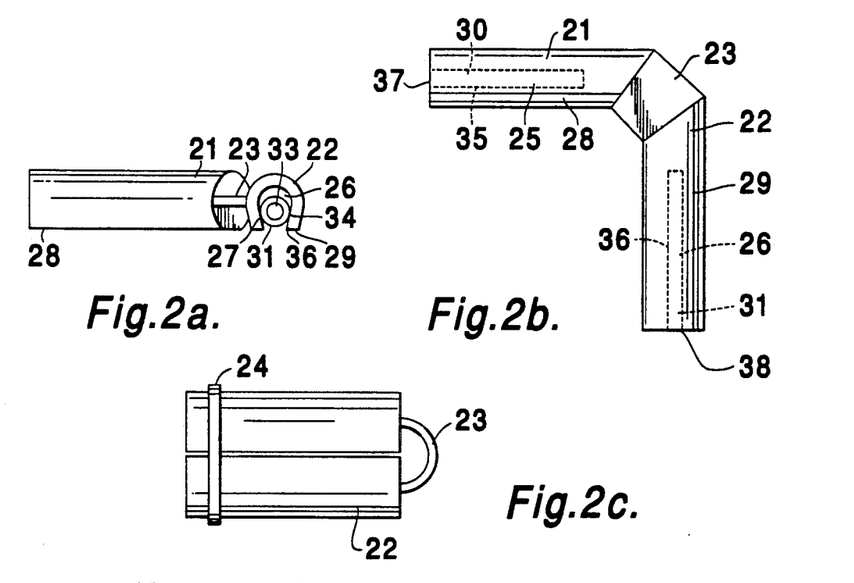
FIGS. 2a, 2b and 2c are plan views of a device, in accordance with a second embodiment of the present invention, in which tubular capsules or capillaries are supported in half cylinders.

FIGS. 2a, 2b and 2c show a device in accordance with a second embodiment of the Present invention in which a pair of half cylinders 21 and 22 are connected by a flat hinge 23 made of resilient material so that the pair of cylinders may be folded together into the configuration shown in FIG. 2c for insertion into the rumen of an animal. Typically, the half-cylinders 21 and 22 and the hinge 23 are composed of an integral body of moulded plastics. The half cylinders 21, 22 may be held in the configuration shown in FIG. 2c by restraining means 24 which surround a portion of the half cylinders 21, 22 and which in the rumen environment are released e.g. by degradation to allow the device to return to the open configuration shown in FIGS. 2a and 2b. The restraining means may be or comprise any material which is dissolved, destroyed, ruptured or broken in the rumen environment. Suitable materials include gelatin string or gelatin tape. Alternatively, the restraining means may comprise water soluble adhesives.

Each half cylinder 21, 22 is provided with a respective longitudinal passageway 25, 26 into which a sealed glass tubule or sealed glass capillary 27 filled with active material is placed. The glass of the tubule or capillary has a $P_2O_5$ content ranging from 40 to 50 mole %. A longitudinal edge of each passageway 25, 26 is disposed in the flat longitudinal surface 28, 29 of the respective half cylinder 21, 22 thereby to provide a respective continuous longitudinal slot 30, 31 in each half cylinder 21, 22 which allows access of the rumen fluid to the glass of the tubule or capillary enclosing the active material 33. A stationary liquid layer 34 is formed in the vicinity of the line of contact between the tubule or capillary 27 and the edge 35, 36 of the slots 30, 31 where there is free access to the rumen fluid along the slots 30, 31. This means that dissolution of the glass of the tubule or capillary occurs in a controlled manner in the region of the stationary liquid layer and when the wall of the tubule or capillary is dissolved away, the active material can easily flow out of the passageway. Although rumen fluid can also enter the passageway 25, 26 via a free open end 37, 38 thereof so as to lie behind the tubule or capillary, controlled and preferential dissolution of the soluble phosphate glass occurs in the region of the stationary liquid layer.

The tubules placed in the passageways can be made with a portion of their walls of a smaller thickness than elsewhere and the tubules positioned so that that portion is placed above the opening of the respective slot. This enables precise control over the release of the active material. In order to obtain pulsed release of e.g. an anthelmintic, tubules or capillaries chosen to release after different elapsed times by having different glass compositions or thicknesses may be placed in one or more devices.

Figure 3:
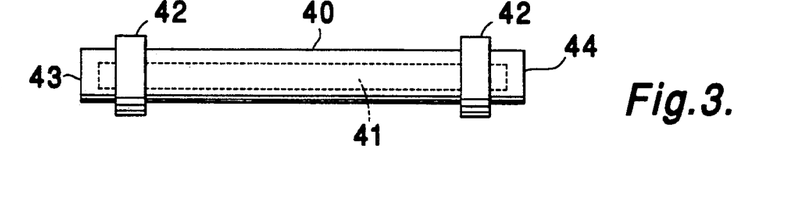
FIG. 3 is a plan view of a device, in accordance with a third embodiment of the present invention, in which a tubular capsule of phosphate glass enclosing an active material is surrounded by a pair of rubber bands.

FIG. 3 shows a device in accordance with a third embodiment of the present invention. The device consists of a sealed glass tubule 40 of soluble phosphate glass having a $P_2O_5$ content of from 40 to 50 mole % and enclosing an active material 41. A pair of rubber bands 42 (or washers or grommets) is placed around the tubule 40. Each rubber band 42 is about 5mm wide and is placed with its centre about 8mm from a respective end 43, 44 of the tubule 40. In use, the tubule 40 is received in a respective passageway 25, 26 of the device illustrated in FIGS. 2a, 2b and 2c instead of the tubule 27 illustrated in those Figures. The rubber bands 42 assist in retaining the tubule 40 securely in the passageways 25, 26. When the device is disposed in an aqueous medium, a stationary liquid layer is retained between each of the rubber bands 42 and the tubule 40. Accordingly, the glass of the tubule 40 dissolves preferentially under the rubber bands 42 in a controlled manner. When the glass of the tubule 40 is perforated as a result of the dissolution, active material 41 can easily flow out of the tubule 40 via the perforation so formed.

The present invention is based on the discovery by the present inventor that in situations where the diffusion of dissolution products away from the vicinity of a $P_2O_5$ containing glass surface is constrained, the dissolution rate is related not only to the composition of the glass but also to the concentration of such products at the glass-solution interface, and the ability controllably to avoid the formation, on the surface of the glass, of a film which can interfere with dissolution. The formation of such a film particularly arises where the aqueous environment contains cations which can form insoluble phosphates e.g. $Ca^{++}$ and $Mg^{++}$. Such environments include hard water and body fluids of animals. Thus it is not only necessary to select a glass composition to get a particular dissolution rate, but also to select conditions for the dissolution of that glass in relation to its glass composition. Such a selection means that the presence of dissolution products in the aqueous medium in the vicinity of that glass surface does not interfere with the dissolution rate. Any such interference will render the selection of accurate time intervals for dissolution impossible.

In the case of glasses with a $P_2O_5$ content below about 40 mole % we have found that the total phosphate ions released when the glass dissolves contain only a small porportion of polyphosphate ions. Consequently, complexing of $M^{++}$ ions in the aqueous medium by polyphosphate ions to produce soluble dissolution products may not take place at a sufficient rate to prevent the build up of the concentration of $M^{++}$ ions adjacent the glass to a value at which film formation of insoluble phosphates occurs adjacent the glass surface. This inhibits dissolution of the glass and reduces the dissolution rate, generally by an unpredictable amount.

For glasses having a $P_2O_5$ content above about 50 mole %, the high proportion of polyphosphate ions in the total phosphate ions released when the glass dissolves tends to result in the formation of gelatinous complexed phosphate films adjacent the glass surface which also reduce the dissolution rate of the glass.

In accordance with the present invention, in order to achieve a controlled dissolution rate the soluble phosphate glasses have a $P_2O_5$ content of from 40 to 50 mole %, preferably from 44 to 48 mole %. We have found that for glasses having a $P_2O_5$ content of from 40 to 50 mole %, the dissolution rate is substantially constant and controllable in any selected set of operating conditions, in particular over a selected concentration range of dissolution products in the stationary liquid layer. In the case of glasses with a $P_2O_5$ content of from about 44 to 48 mole %, we have found that the dissolution rate is independent of the concentration of the dissolution products over a wide range from about 30ppm to 30000 ppm. The dissolution rate remains constant since the release of polyphosphate ions is such as to complex the $M^{++}$ ions as fast as they arrive by diffusion from the bulk solution as well as the $M^{++}$ ions released from the glass itself. As one moves towards 50 mole % $P_2O_5$, the tendency for gelatinous films to form increases. As one moves below 45 mole % $P_2O_5$, the tendency for dissolution products to separate, from a deposit and interfere with dissolution increases and the dissolution rate can only be controlled by a more careful control of the concentration of dissolution products. It is believed that this is due to the inability of the dissolution products, which in the case of the lower $P_2O_5$ content glasses are primarily relatively short chain phosphate anions, to complex with ions such as $Ca^{++}$ to form soluble complexes. This results in insoluble phosphate products forming a continuous or semicontinuous layer on the glass surface and reducing the dissolution rate at that surface. Moreover, the dissolution rate may decrease with time as the film becomes thicker so that it is not possible to achieve a time - independent solution rate. As the solution rate becomes more dependent on the concentration of the solution products it becomes necessary to maintain control of the concentration of the dissolution products at the glass/liquid interface within fairly narrow limits to achieve a predictable dissolution rate.

Suitable glass compositions in the range 40 to 49 mole % $P_2O_5$ for use in the devices of the present invention disclosed above are shown in Table I below. It is preferred to minimize the use of $Al_2O_3$ as we have found that glasses containing more than 1.5 mole % $Al_2O_3$ do not give as consistent a performance as glasses in which the dissolution rate is varied using other materials such as CaO, MgO and ZnO. The glass compositions may contain components to tint the glass, different tints being chosen to indicate different dissolution rates. Any standard glass colouring oxide can be used. The concentration is normally less than 0.5 mole %. Suitable oxides are e.g. nickel oxide or manganese oxide.

TABLE I

| | All glass compositions in Mole % | | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| $P_2O_5$ | 40 | 45 | 45 | 45 | 45 | 45 | 45 | 45 | 45 | 45 | 45 | 44.8 | 47 | 49 | 45 | 45 | 45.0 |
| CaO | 22 | 20 | 9 | 24 | 18 | 16 | 14 | 12 | 10 | 22 | 14 | 22.1 | 20 | 18 | 6.0 | 6.3 | 6.15 |
| $Na_2O$ | 38 | 35 | 39 | 31 | 35 | 35 | 35 | 35 | 35 | 33 | 39 | 33.1 | 33 | 33 | 39.0 | 39.0 | 39.0 |
| MgO | — | — | 3 | — | 2 | 4 | 6 | 8 | 10 | — | 2 | — | — | — | 6.0 | 6.5 | 6.5 |
| ZnO | — | — | 3 | — | — | — | — | — | — | — | — | — | — | — | 3.0 | 3.0 | 3.0 |
| MnO | — | — | 1 | — | — | — | — | — | — | — | — | — | — | — | 1.0 | 0 | 0 |
| $Al_2O_3$ | — | — | — | — | — | — | — | — | — | — | — | — | — | — | 0 | 0.2 | 0.35 |

As indicated above, the dissolution rate is related to the concentration of dissolution products at the glass/solution interface. It is well known that when a solid surface is Present in a moving liquid there is always a thin, stationary film of this liquid held at the solid/liquid interface. The thickness of this thin film is an inverse function of how fast the bulk of the liquid is circulating and/or flowing past the solid surface at that point. The products of dissolution of the solid in the liquid are transported away from the solid surface to the bulk solution by diffusion through this film and any species in solution in the bulk solution are transported to the solid surface by diffusion through this film. It follows that the thinner this film, the lower will be the concentration of solution products at the solid-liquid interface. In a well-stirred liquid this stationary liquid film will be very thin, transport of dissolution products through it very fast and, consequently the concentration of dissolution Products at the solid-liquid interface is very low an the concentration at the solid-liquid interface of species present in the bulk solution is near to that of the bulk solution. In accordance with the present invention it is provided that the dissolution of the phosphate glass in the device of the invention occurs under such conditions that the thickness of the stationary liquid film is independent of the flow conditions in the bulk liquid. A uniform stationary liquid film thickness is maintained over the area where dissolution is occurring so that the rate at which the glass is dissolving, and the rate of diffusion of dissolution products out of the film, are at a value where the concentration of dissolution products in the film remains in the range where the dissolution rate for that particular glass remains substantially constant. In a steady state, the rate of diffusion of the products across the boundary between the surface film of the liquid and the bulk liquid will be equal to the rate at which the glass is dissolving. For any particular initial film thickness selected as described below, knowing the glass dissolution rate and the rate of removal of dissolution products by diffusion it is possible to calculate the concentration of dissolution products at the glass-liquid interface and also knowing the concentration of ion-species in the bulk solution it becomes possible to check whether the choice of a particular liquid film thickness results in a concentration in the desired range for a particular glass.

In the three illustrated embodiments, the initial liquid film thickness is selected by control of the spacing between the end wall and the glass disc in the embodiment of FIG. 1; by the juxtaposition of the tubule and the passageway in the embodiment of FIG. 2; and by the placing of the rubber bands around the tubule in the embodiment of FIG. 3. The diffusion is controlled by providing a barrier which allows any escape from the constrained film to be by means of diffusion at a rate such that the concentration of the solution products in the film remains in the desired range. In other embodiments, the initial liquid film thickness may be selected by providing a thin water permeable barrier such as filter paper, a solid plate with holes, or a mesh to constrain the liquid film in place. In the embodiment of FIG. 3, preferential dissolution in a narrow band encircling the tubule in the region of the grommet at a faster rate than elsewhere can result in the tubule breaking apart at one or more places releasing its contents. The trapped film thickness will of course increase as the glass dissolves to that e.g. with a 2 mm thick soluble phosphate glass an initial choice of film thickness of 2.5 mm would increase to 4.5 mm. We have found that any such change in film thickness does not produce an adverse change in the concentration of the solution products so as to interfere with the uniform dissolution of the glass surface exposed to the aqueous solution.

The actual dimensions of a device are determined by the volume of active material such as e.g. an anthelmintic which it is desired to release from the device on dissolution of a glass retaining member e.g. in the form of a disc, or a wall of a capillary, and the elapsed time before that release takes place after immersion in the aqueous medium. The actual dissolution rate and the concentration of dissolution products needed to maintain substantially that actual dissolution rate can be set down for any situation. As broad criteria we have found with dissolution rates ranging from 0.05mg/cm$^2$/h to 5.0 mg/cm$^2$/h (i.e. ranging over 2 orders of magnitude), a glass with a composition in the range from 40 to 50 mole % $P_2O_5$ will dissolve consistently if the concentration of solution products is maintained in the range 0.1 to 6 g/l. It is possible for the man skilled in the art designing a device which has a particular elapsed time before release of the active material at least to determine on a theoretical basis, an approximate film thickness for a particular glass having a known dissolution rate. Starting from that basis, the man can then determine experimentally the exact dimensions of the device needed to ensure a satisfactory layer thickness. For the dissolution process, in the steady state which is promoted by the existence of the stationary liquid layer, the rate of diffusion of dissolution products across the boundary between the stationary liquid layer and the bulk liquid is given by:

$$R_{Boundary} = D \frac{C_s}{x}$$

where D is the diffusion constant, $C_s$ is the concentration of solution products at the surface of the glass, x is the thickness of the stationary liquid layer and the concentration of solution products in the bulk liquid is assumed to be zero. In the steady state, $R_{Boundary}$ is equal to the rate R at which the glass is dissolving. From the equation it is possible to determine x, knowing R and $C_s$, and $C_s$ knowing R and x. The devices of the invention when used e.g. to release anthelmintics could have production runs running in excess of several million, and hence the experimental work to define exact dimensions for a device so as to achieve Particular release characteristics is justifiable. Even such a device would probably go through several prototypes before the production version was approved.

Experimental results illustrating the present invention will now be described.

A number of the glass compositions specified in Table 1 were examined as described below in order to determine the various dissolution parameters and mechanisms.

In order to demonstrate the effect of the concentration of the solution products in the liquid surrounding a phosphate glass, the solution rates of the above glasses were examined under different conditions. The solution rates were determined by measuring the loss of weight of a sample. Samples were simply removed at intervals from the solution and blotted dry with paper tissue.

Figure 4:
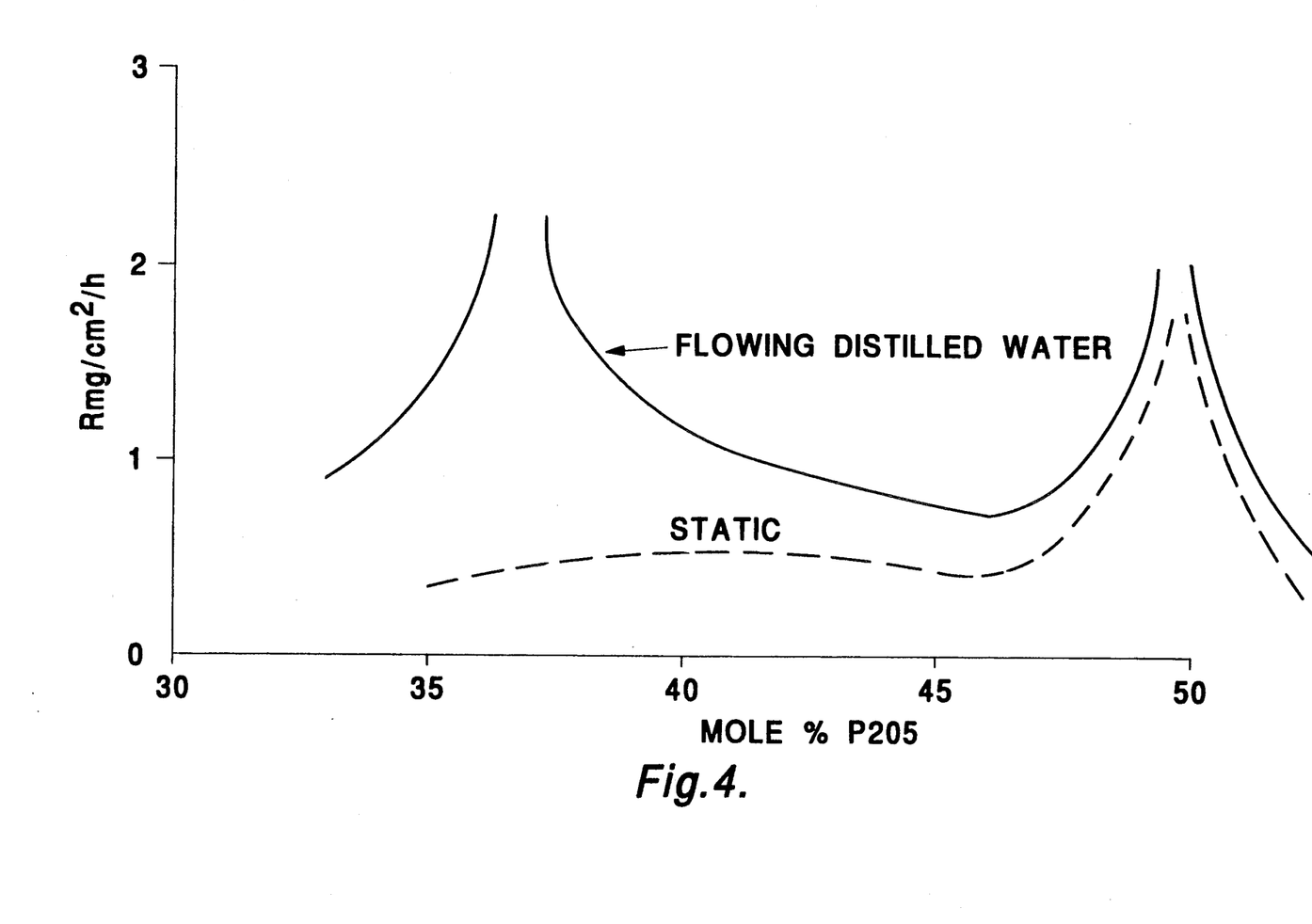
FIG. 4 is a graph showing the relationship between dissolution rate and molar percent of $P_2O_5$ for a series of glass compositions.

FIG. 4 is a graph showing the relationship between the dissolution rate R(mg cm$^{-2}$h$^{-1}$) at 38° C. and the molar Percent of $P_2O_5$ for a series of glass compositions. The dissolution rate was measured by suspending samples in an open neck nylon bag in liquid. The amount of $P_2O_5$ varied between 30 and 55 mole %. The amount of CaO with compositions was a constant 23 mole % and the remainder of each composition comprised $Na_2O$.

The graph shows the results for flowing distilled water and for static distilled water. The pH varied between notional limits of pH 5 to 8 due to the effects, inter alia, of dissolved atmospheric $CO_2$ in the water, and ionic concentrations.

In flowing distilled water, all glass compositions exhibit a controlled dissolution behaviour i.e. the value of R is reproducible and a unique function of the glass composition. This is because there are sufficient polyphosphate ions to complex the small amount of $M^{++}$ ions present, namely those emanating from the glass, and a time - independent steady - state dissolution rate is established.

In static distilled water, the value of R varies in a roughly similar manner to that in flowing distilled water but is reduced since there tends to be a higher concentration of $M^{++}$ ions at the surface of the glass leading to the formation of phosphates which inhibit dissolution.

Thus the dissolution behaviour of a phosphate glass can be influenced by choice of composition in relation to the environment in which it is to be used.

Although not illustrated in a graph, we have found that in flowing hard tap water, the value of R is an order of magnitude or more lower than the value in flowing distilled water for glasses of the same composition. This value can change under certain conditions with elapsed time, and such changes can be abrupt. This is believed to be due to the presence of free $M^{++}$ ions in the liquid layer adjacent to the glass surface which react with ortho- and pyro-phosphate ions released from the glass surface to form compounds with a low solubility product. The formation of these compounds can result in a continuous film being deposited on the glass, and the rate limiting process becomes the diffusion through this slightly permeable layer. Abrupt changes can then occur when there is an alteration of the integrity of the film. Film formation occurs, it is believed, when the water is sufficiently hard that there is a continuous supply of $M^{++}$ ions to the glass in excess of the ability of the polyphosphates released from the glass to complex these ions to form soluble complexes. In a limited volume of hard water, the behaviour is dependent on the value of the dissolution rate R, and the most extreme type of behaviour is observed for glasses with values of the dissolution rate less than 0.1 mg/cm/$^2$/h. The value of R falls as the insoluble phosphate film builds up, and continues at this reduced rate until sufficient polyphosphates are dissolved from the glass to complex all the $M^{++}$ ions present in the solution.

In the case of glasses with $P_2O_5$ 44 to 50 mole % and very low R, the surface film may persist for very long periods when the glass is exposed to hard water because of the low rate of release of polyphosphate complexing ions into the solution. Care should be therefore taken in choosing a glass for operating in hard water conditions to choose a composition with an R higher than about 0.1 in order to avoid such effects. This may mean using a device with a greater thickness of glass in order to achieve a particular elapsed time for the release of an active material. Alternatively polyphosphate ions may be provided from some other source such as a sacrificial supply of glass with a composition chosen to give an adequate release of polyphosphate ions rapidly to complex the $Ca^{++}$ and $Mg^{++}$ ions initially present in the stationary liquid layer. This can be done by e.g. combining solid rods or granules of glass as an integral part of any device.

Figure 5:
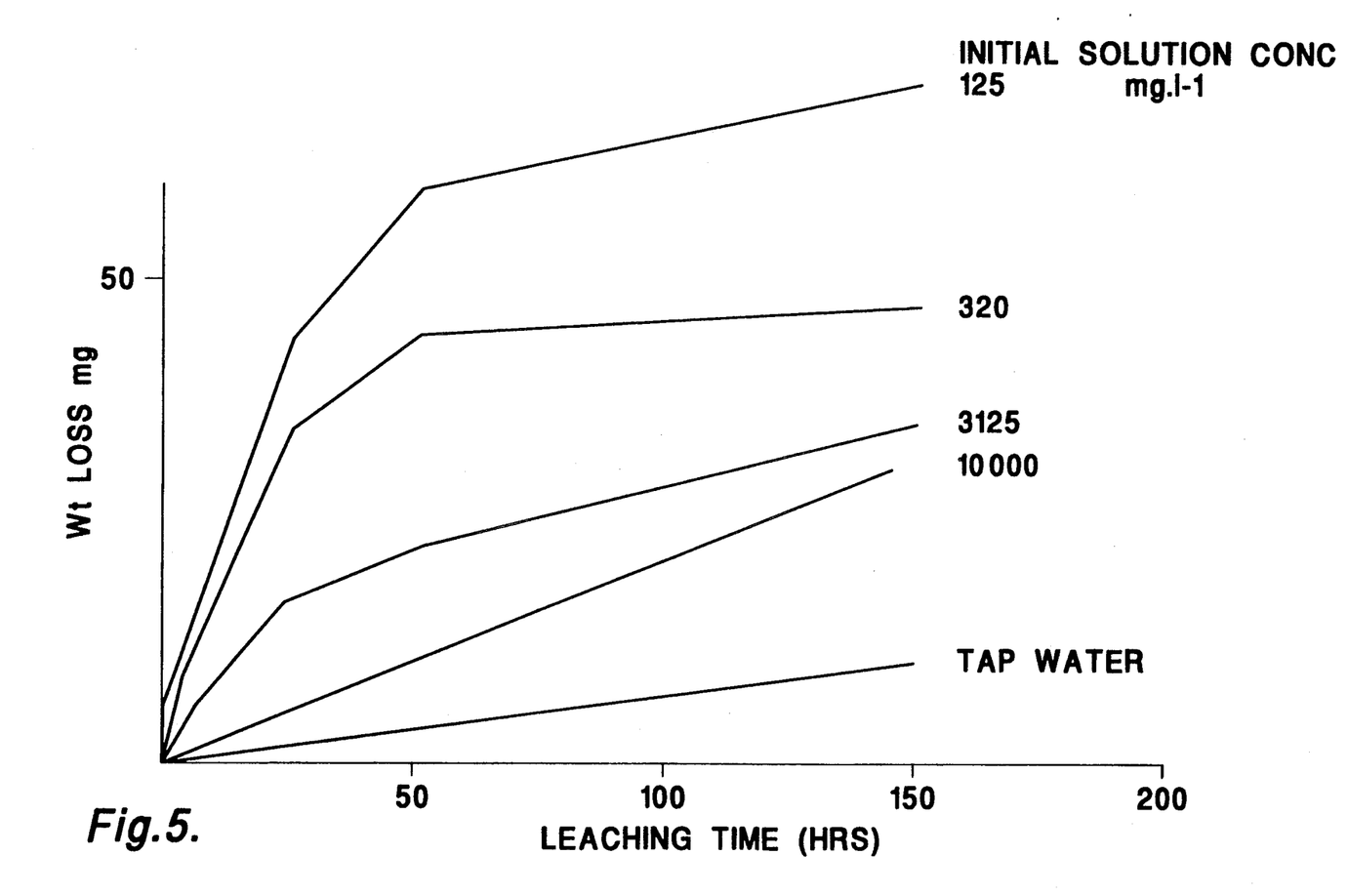
FIGS. 5 to 8 are each a graph showing the relationship between weight loss and leaching time for a respective series of glass compositions.

FIG. 5 is a graph showing the relationship between weight loss (in mg) and leaching time (in hours) for a series of five flat buttons made of a glass of composition in mole % $P_2O_5$ 40, CaO 22, $Na_2O$ 38. The buttons of glass were cut 2 to 4 mm thick from a rod of about 1 cm diameter and were supported vertically in 40 ml unstirred solvent at 38° C. This was done by supporting the buttons between two pins on a rubber bung. The solvent is water, in four cases distilled water containing a selected initial concentration of the solution products of the glass under test and in one case being tap water (Hardness 340 ppm $Ca^{++}$).

The solution was static and the concentration of the dissolution products increased with time.

The graph shows that with $P_2O_5$ at 40 mole %, for relatively low initial concentrations of dissolution products (i.e. initial concentrations of 125, 320 and 3125 mgl$^{-1}$), the dissolution rate R (which is related to the slope of the lines) is initially high but falls off as the concentration of solution products increases with time. Also, there is no concentration region in which R is independent of solution concentration. For a high initial concentration of dissolution products (i.e. initial concentration of 10000 mgl$^{-1}$) and tap water, the dissolution rate R is too low for practical use, the rate being limited by the diffusion of water and dissolution products through the insoluble phosphate film which forms on the glass surface.

Thus for phosphate glasses having 40 mole % $P_2O_5$, the dissolution rate rate can vary greatly depending on the concentration of dissolution products in the aqueous solution.

Figure 6:
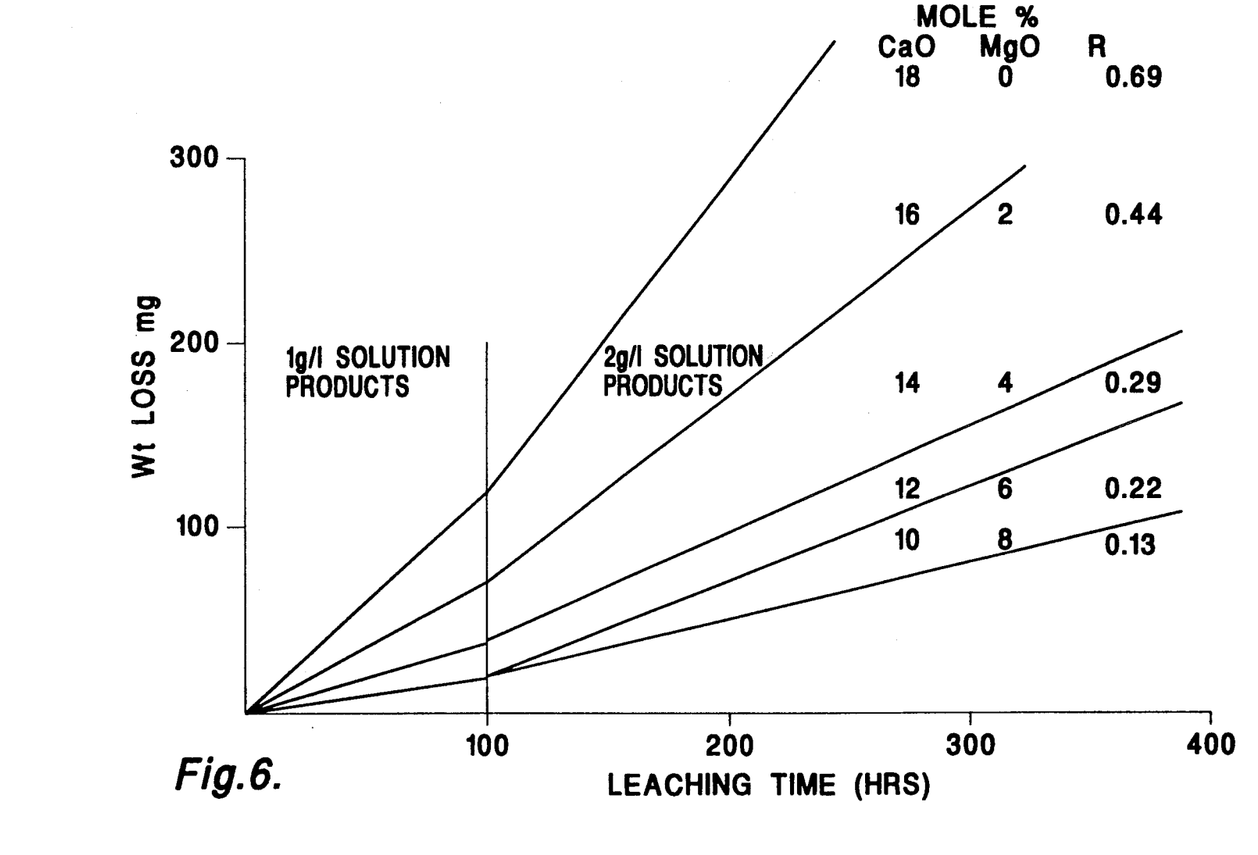

FIG. 6 is a graph showing the relationship between weight loss (in mg) and leaching time (in hours) at 38° C. for a series of five buttons similar to those described above which were made glasses containing a constant amount of $P_2O_5$ 45 mole %, and a constant total of MO (where MO=CaO+MgO) at 18 mole %, and $Na_2O$ 37 mole %. The glass were varied in composition from the MO content being solely CaO to CaO being 10 mole % and MgO 8 mole %, by replacing CaO by MgO in 2 mole % steps. The buttons after etching were placed initially in 40 ml of tap water containing 1g/litre of solution products and this was maintained substantially constant for 100 hours, and the concentration was then increased to a substantially constant 2g/l for the remainder of the experiment. The solution was static.

FIG. 6 shows that with a steady concentration of dissolution products, the value of R varies with the amount of MgO and CaO in the glass. The Figure also shows that R (related to the gradiant of each line) is substantially constant for each glass at each concentration of dissolution products examined. The small variation in the dissolution rates being the two different concentrations is due, inter alia, to changes in the pH of the solution which can vary with the concentration and also depends on the glass composition employed. Thus for a given phosphate glass composition having 45 mole % $P_2O_5$, the dissolution rate R does not vary substantially as a result of changes in concentration of the dissolution products in the aqueous solution.

Figure 7:
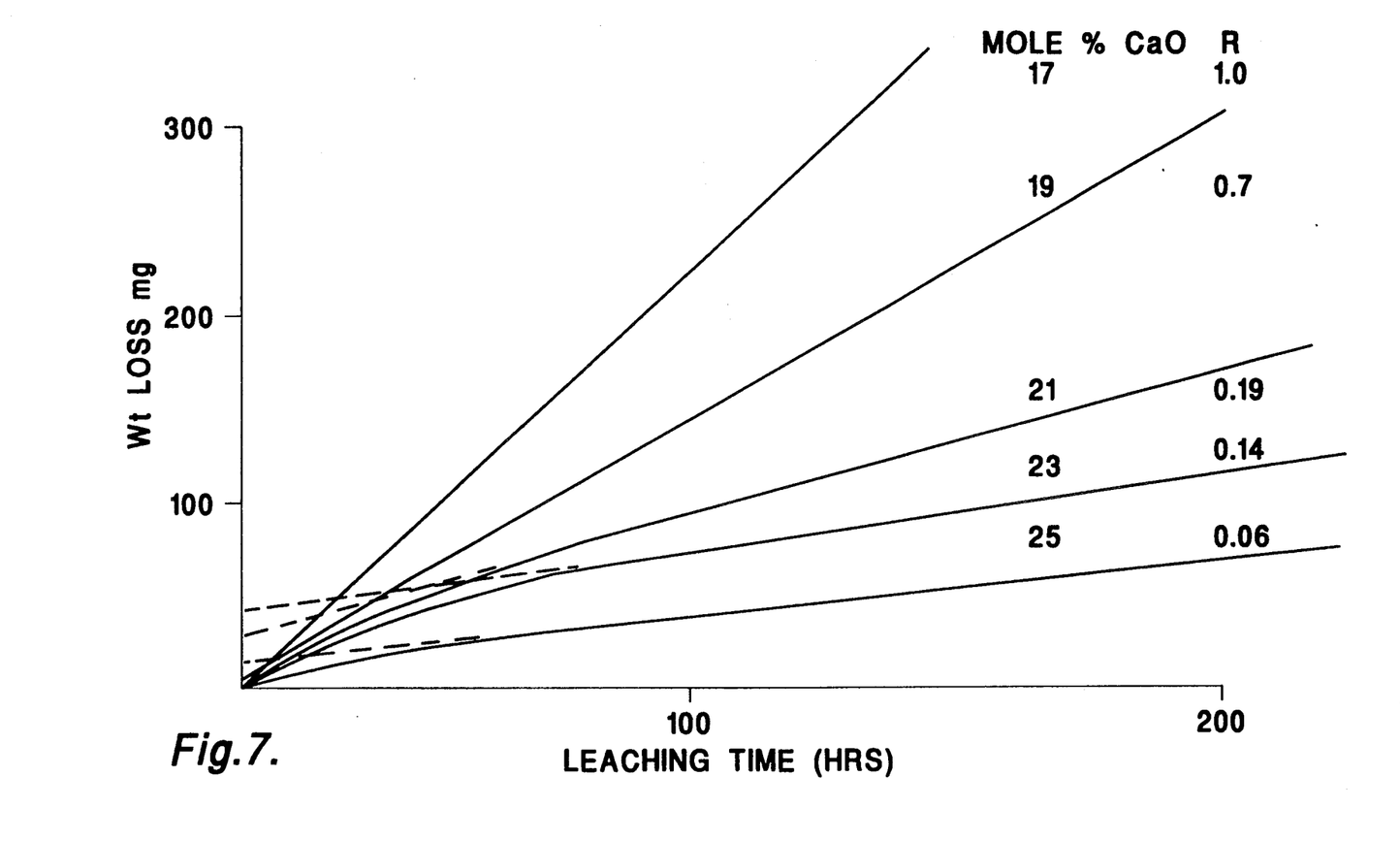
Figure 8:
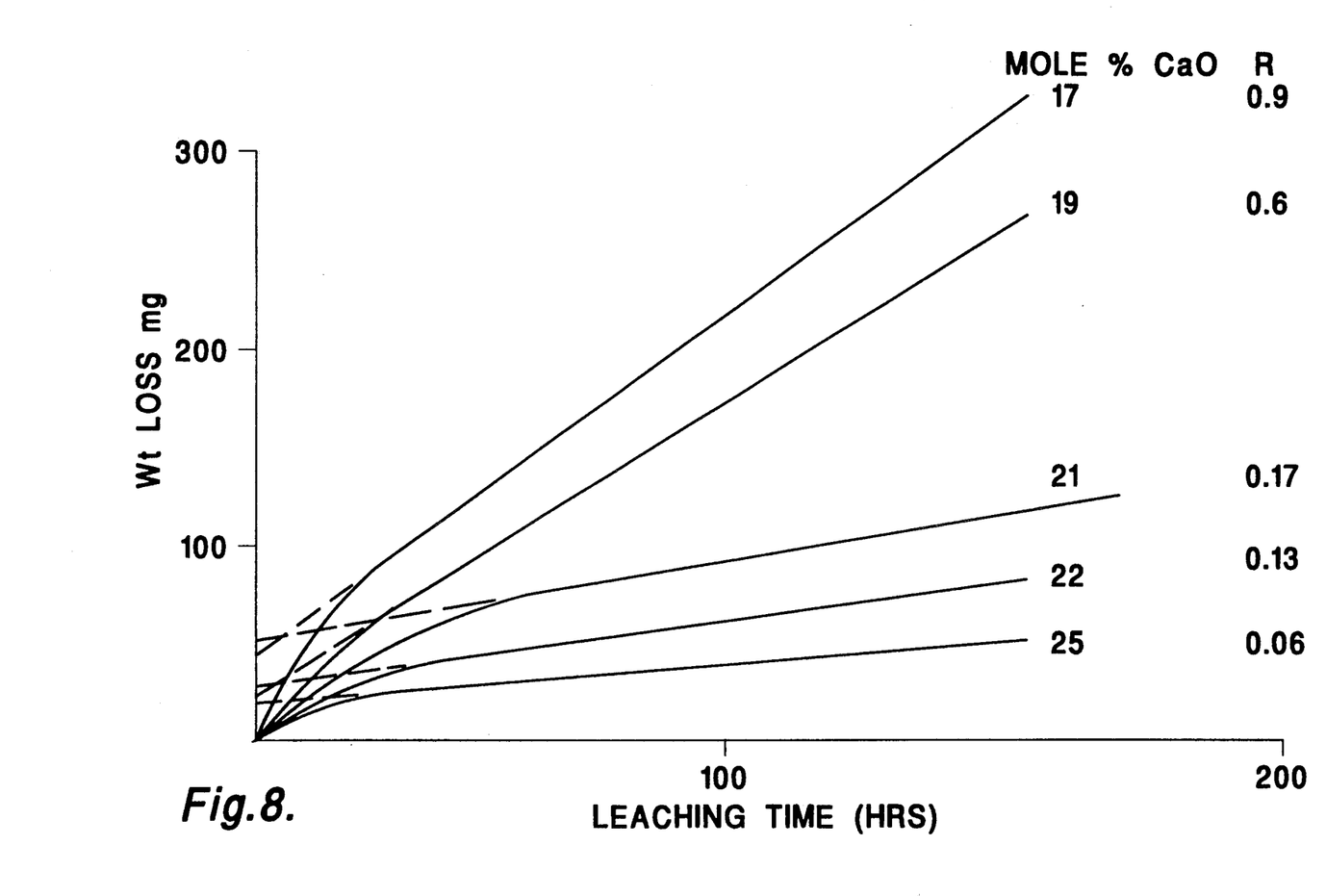

FIGS. 7 and 8 are graphs showing the relationship between weight loss (in mg) and leaching time (in hours) for a further series of five buttons in different respective dissolution conditions.

In the experiment of FIG. 7, a series of five buttons were made, the buttons being comprised of a glass containing a constant amount of $P_2O_5$ at 45 mole %, and an amount of CaO varying in steps of 2 mole % from 17 to 25 mole %, with a fall of $Na_2O$ content from 38 mole % to 30 mole %. The buttons were placed in 40 ml of distilled water containing 10 g/l as a fixed initial amount of solution products, and the weight in mg was measured against time. The concentration of dissolution products was maintained substantially constant. The liquid was static. The results were plotted as weight loss against time for each glass, and the dissolution rate (R) calculated.

In the experiment of FIG. 8, a further set of five buttons, the same as those used in the experiment whose results are given in FIG. 7, were examined under conditions in which the buttons were placed in 40 ml distilled water with no change in the aqueous solution being made during the course of measurements so that dissolution products built up in the solvent. The solvent was static. Weight loss in mg was then plotted against time and the dissolution rate (R) calculated for each glass.

FIGS. 7 and 8 show that for a phosphate glass containing 45 mole % $P_2O_5$ the dissolution rate for any given glass under either of the conditions is substantially constant (i.e. the gradient of each line is substantially constant, apart from an initial start-up period before a steady state is reached). Those Figures also show that for any given glass composition containing 45 mole % $P_2O_5$, the value of R is substantially the same whether the dissolution products remain at a constant concentration (FIG. 7) or are allowed to increase in concentration as dissolution continues (FIG. 8). Thus phosphate glasses having 45 mole % $P_2O_5$ have dissolution rates which are relatively independent of the concentration of dissolution products in the aqueous solution.

In FIGS. 7 and 8, the initial start-up period in which the gradient is not linear results from the initial state of the glass buttons. If the glass buttons are cut from a rod, the surface of the buttons will have irregularities on the cut surface. The influence of such irregularities on the dissolution rate was studied by preparing two samples of the same glass composition, one sample being as cut, and the other being etched before immersion in the solvent to reduce the thickness of the button by at least 0.2 mm as measured by a micrometer thereby to remove irregularities on the cut surface. Each sample button had the same glass composition in mole % of $P_2O_5$ 45, MgO 2, CaO 14 and $Na_2O$ 39. The buttons were immersed in 40 ml distilled water at 38° C., with no change being made to the dissolved products composition during course of the measurements so that the dissolution products built up in the solvent. The results are shown in FIG. 9 which is a graph illustrating the relationship between weight loss (in mg) and leaching time (in hours).

Figure 9:
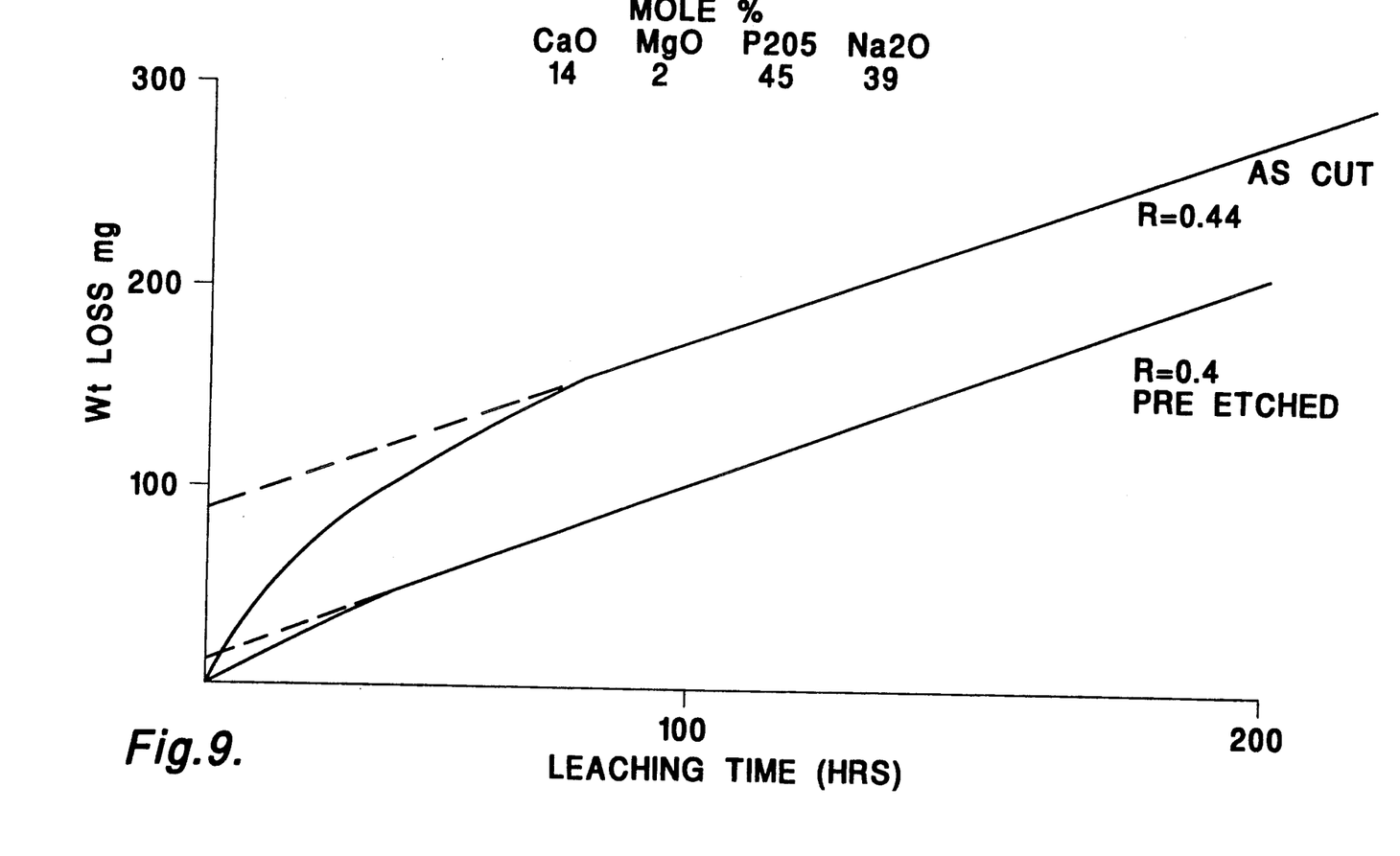
FIG. 9 is a graph showing the relationship between weight loss and leaching time for two differently prepared samples of the same glass composition.

FIG. 9 simply demonstrates that when a glass is etched to remove the rough surface, the initial high rate of dissolution is not observed, and that the steady values of R are the same for each glass. This shows that for controlled dissolution it is important to be aware of this initial high rate if use of glasses with damaged surfaces cannot be avoided. This is consistent with FIGS. 7 and 8 wherein the initial high dissolution rates represented by the curved portions of the plots were due to the presence of cut surfaces on the buttons.

Figure 10A:
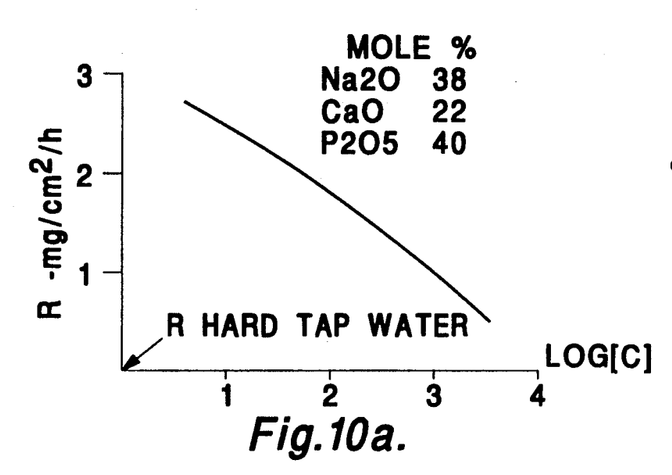
FIGS. 10a to 10g are graphs showing the relationship between the dissolution rate and the logarithm of the concentration of the dissolution products in the aqueous medium for a series of glass compositions.
Figure 10B:
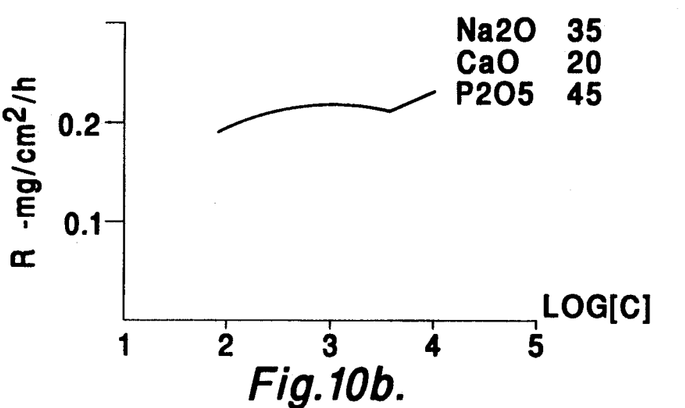
Figure 10C:
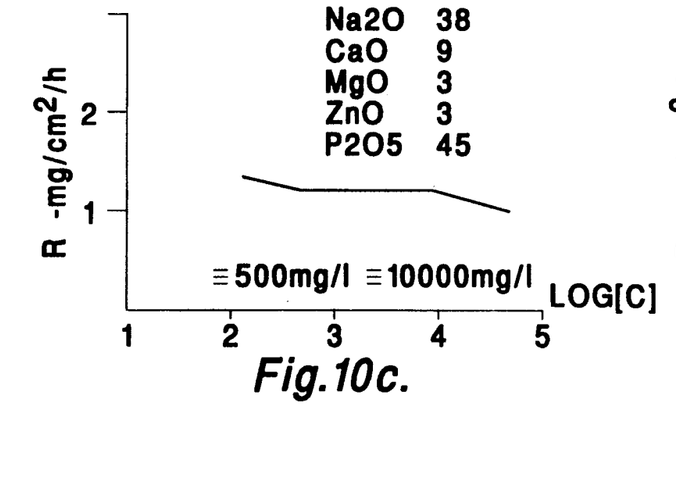
Figure 10D:
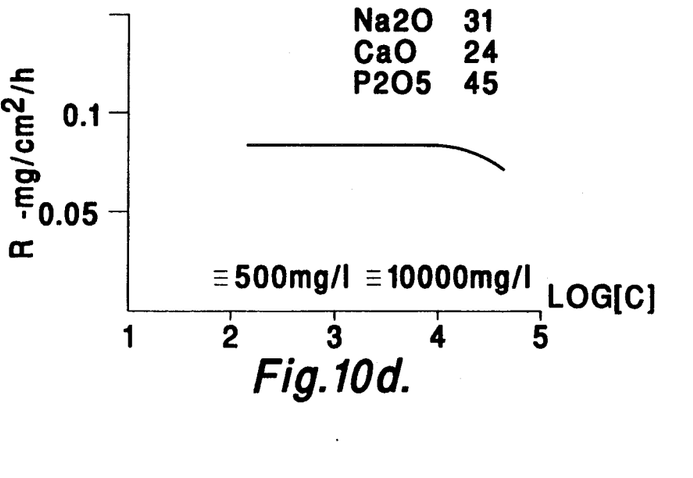
Figure 10E:
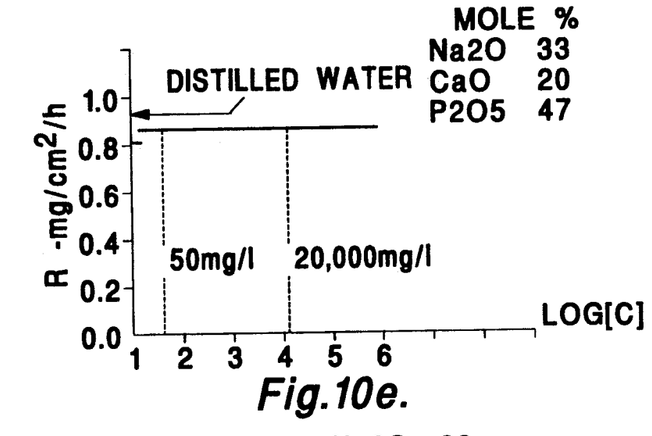
Figure 10F:
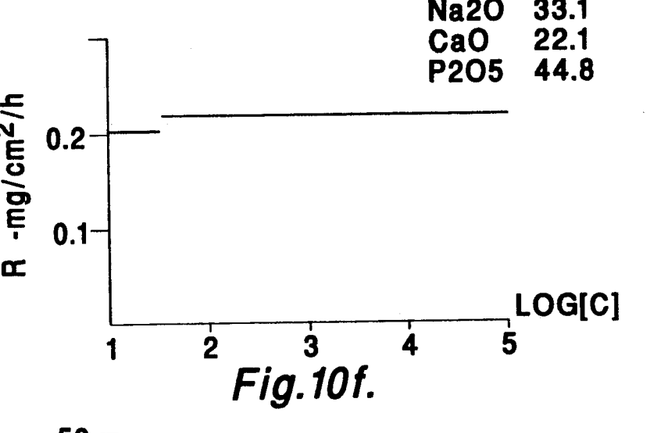
Figure 10G:
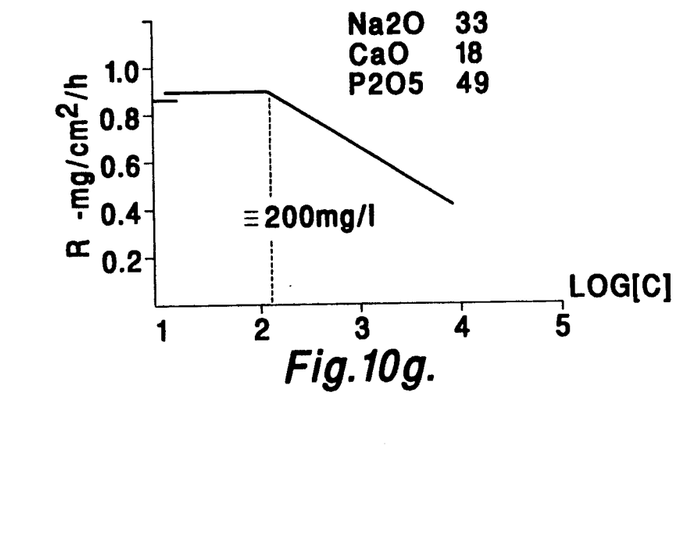

FIGS. 10a to 10g are graphs showing the relationship between the dissolution rate R (in mg $cm^{-2}h^{-1}$) at 38° C. and the logarithm of the concentration of the solution products (in mg $l^{-1}$) for a variety of soluble phosphate glass compositions. FIG. 10a demonstrates that with $P_2O_5$ at 40 mole %, as the concentration of dissolution products increases with time, there is a falling off in the value of R, and there is no concentration region in which R is independent of solution concentration. This is consistent with the three upper lines in FIG. 4. Hence if one wishes to achieve a reasonably constant dissolution rate with a 40 mole % $P_2O_5$ glass it is essential in this case to avoid the concentration of dissolution products building up in the region of the glass surface, and to keep that concentration at a leval where the desired dissolution rate can be achieved. It is clearly preferable if possible to avoid working in this glass-composition region unless accurate control of the concentration of dissolution products can be achieved and the glass chosen has the desired dissolution rate under those conditions. One situation where it would be possible to work with glasses of about 40 mole % $P_2O_5$ is where the water was naturally soft or was artificially softened so as to be substantially free of calcium and magnesium ions.

As the glass composition varies from 40 to about 44 mole % $P_2O_5$, this requirement to have a carefully controlled specific concentration of dissolution products is reduced and it is possible to get a substantially controlled dissolution rate over a narrow concentration range.

As the glass composition reaches 44 mole % $P_2O_5$ and above, there is a fairly broad concentration range which still provides a substantially constant dissolution rate.

FIGS. 10b to 10g demonstrate that for glasses of differing compositions between 44.8 and 49 mole % $P_2O_5$, the dissolution rate R is substantially constant with varying concentration of dissolution products in the solvent over a particular concentration range. This is represented by the flat portion of the plot. It should be noted that the actual value of R varies greatly between different glass compositions.

Figure 11:
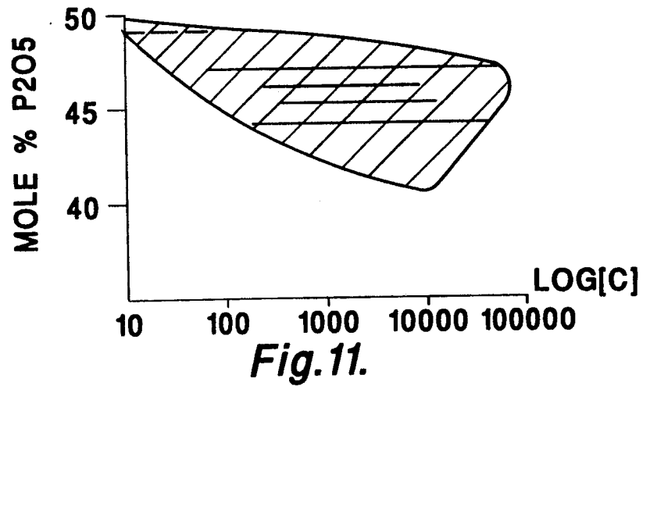
FIG. 11 is a graph showing the relationship between the molar amount of $P_2O_5$ and the logarithm of the concentration of the dissolution products in the aqueous medium.

FIG. 11 is a graph showing the relationship between the mole % $P_2O_5$ in the glass compositions of FIGS. 10a to 10g and the logarithm of the concentration —the graph having been compiled from the data of FIGS. 10a to 10g. It may be seen that for each glass composition there is a concentration range in which R is independent ($+5\%$) of concentration, each range being respectively represented by a horizontal straight line. The horizontal straight lines together define an approximate area, which is shown hatched, which defines a region wherein for any given $P_2O_5$ molar amount the value of R does not substantially vary over the relevant concentration range. Thus, when designing controlled delivery devices in accordance with the present invention, if one selects a particular molar percentage of $P_2O_5$ for the glass composition it is possible to determine within which concentration range the device must be employed in order to obtain a substantially constant dissolution rate. It will be seen from FIG. 11 that as the value of $P_2O_5$ approaches 50 mole %, the region where R is constant becomes limited in size and as $P_2O_5$ approaches 40 mole % the region becomes vanishingly small.

What I claim is:

1. A device for controllably delivering an active material into an aqueous medium, the device comprising a soluble phosphate glass to form a barrier layer between the active material and the aqueous medium, the barrier layer defining a wall of a chamber containing the active material, which wall is breached as a result of dissolution thereof over a particular period of time thereby to deliver into the aqueous medium the active material which is retained in the device, the soluble phosphate glass having a $P_2O_5$ content of from 40 to 50 mole %, and a perforated plate which is located in the vicinity of the barrier layer and which is arranged, in use, to constrain a substantially stationary liquid layer between the barrier layer and the perforated plate.

2. A device according to claim 1 wherein the soluble phosphate glass has a $P_2O_5$ content of from 44 to 48 mole %.

3. A device for controllably delivering an active material into an aqueous medium, the device comprising at least one part of a sealed tubular capillary of soluble phosphate glass which encloses the active material, the said at least one part forming, in use, a barrier layer between the active material and the aqueous medium, which said at least one part is breached as a result of dissolution thereof over a particular period of time thereby to deliver into the aqueous medium the active material which is retained in the device, the soluble phosphate glass having a $P_2O_5$ content of from 40 to 50 mole % and a capillary holding means including a passageway which receives the sealed tubular capillary, at least one part of the holding means which defines the passageway being adjacent the said at least one part of the capillary and being arranged in use, to constrain a substantially stationary liquid layer between the said at least one part of the capillary and said at least one part of the holding means.

4. A device according to claim 3 wherein the said at least one part of the holding means comprises a pair of opposed edges of a longitudinal slot of the passageway and the said at least one part of the capillary comprises a pair of longitudinal regions of the capillary which are adjacent the said edges.

5. A device according to claim 3 wherein the capillary holding means includes two passageways, each of which receives a respective capillary.

6. A device according to claim 4 wherein the capillary holding means includes two passageways, each of which receives a respective capillary.

7. A device according to claim 5 wherein each passageway is defined in a respective arm of the capillary holding means and further comprising hinge means which is connected between the two arms and is adapted to permit the arms to be moved between adjacent and remote positions.

8. A device for controllably delivering an active material into an aqueous medium, the device comprising at least one circumferential part of a sealed tubular capillary of soluble phosphate glass enclosing the active material, the said at least one part forming, in use, a barrier layer between the active material and the aqueous medium, which said at least one part is breached as a result of dissolution thereof over a particular period of time thereby to deliver into the aqueous medium the active material which is retained in the device, the soluble phosphate glass having a $P_2O_5$ content of from 40 to 50 mole %, and at least one ring member which surrounds the said at least one part thereby, in use, to constrain a substantially stationary liquid layer between the said at least one part and at least one ring member.

9. A device according to claim 8 wherein the ring member is composed of rubber.

10. A device according to claim 8 further comprising a capillary holding means including a passageway which receives the capillary.

11. A device according to claim 10 wherein the capillary holding means includes two passageways, each of which receives a respective capillary.

12. A device according to claim 11 wherein each passageway is defined in a respective arm of the capillary holding means and further comprising hinge means which is connected between the two arms and is adapted to permit the arms to be moved between adjacent and remote positions.

13. A device for controllably delivering at least one active material into an aqueous medium comprising:
  (i) two sealed capillary tubes comprised of a soluble phosphate glass having a $P_2O_5$ content ranging from 40 to 50 mole % which encloses an active material and which upon usage in an aqueous environment provides a barrier layer between the active material and the aqueous medium which becomes breached as a result of dissolution of the glass after a fixed period of time;
  (ii) two capillary holding means which each comprise a passageway open to the aqueous medium and each of which contains one of said sealed capillary tubes, whereby during usage a substantially stationary layer of the aqueous medium is constrained in the vicinity of a line of contact between the capillary tube and the holding means; and
  (iii) a member which provides for the connection of said two capillary holding means.

14. The device of claim 13 wherein the two capillary holding means each comprise a half-cylinder.

15. The device of claim 14 wherein the connecting member which connects the two half-cylinders is a resilient flat hinge which permits the folding together of said half-cylinders into a closed configuration.

16. The device of claim 15, which further includes a restraining means which surrounds at least a portion of the half cylinders and is comprised of a material which provides for the separation of said half-cylinders into an open configuration when the device is placed in an aqueous environment.

17. The device of claim 16 wherein the restraining member comprises a material which becomes dissolved, destroyed, ruptured or broken in an aqueous environment.

18. The device of claim 17 wherein the material comprises gelatin string, gelatin tape or a water-soluble adhesive.

* * * * *